United States Patent
Lo et al.

(10) Patent No.: US 7,556,780 B1
(45) Date of Patent: Jul. 7, 2009

(54) DEVICE FOR $^{123}$I-ADAM AND AUTOMATIC MANUFACTURING DEVICE THEREOF

(75) Inventors: Ai-Ren Lo, Taipei (TW); Chia-Chieh Chen, Jhongli (TW); Tseng-Chung Huang, Jhongli (TW); Hung-Chun Kao, Shulin (TW)

(73) Assignee: Atomic Energy Council-Institute of Nuclear Energy Research, Taoyuan County (TW)

( * ) Notice: Subject to any disclaimer, the term of this patent is extended or adjusted under 35 U.S.C. 154(b) by 37 days.

(21) Appl. No.: 11/518,442

(22) Filed: Sep. 11, 2006

(51) Int. Cl.
*B01J 19/00* (2006.01)

(52) U.S. Cl. .......................... 422/130; 422/99; 422/129

(58) Field of Classification Search .................. 422/62, 422/99–104, 129, 130; 436/179, 180
See application file for complete search history.

(56) References Cited

U.S. PATENT DOCUMENTS

| | | | | |
|---|---|---|---|---|
| 4,430,319 A * | 2/1984 | Blau et al. | .................. | 424/1.85 |
| 5,130,117 A * | 7/1992 | Kung | ........................ | 424/1.85 |
| 5,200,169 A * | 4/1993 | Wilbur et al. | ............... | 560/104 |
| 5,302,700 A * | 4/1994 | Zalutsky et al. | .......... | 530/391.5 |
| 5,312,592 A * | 5/1994 | Andersson | .................... | 422/61 |
| 5,389,339 A * | 2/1995 | Petschek et al. | ............... | 422/64 |
| 5,808,020 A * | 9/1998 | Ferrieri et al. | ............. | 536/18.5 |
| 5,932,178 A * | 8/1999 | Yamazaki et al. | ........... | 422/159 |
| 6,172,207 B1 * | 1/2001 | Damhaut et al. | ......... | 536/18.4 |
| 6,567,492 B2 * | 5/2003 | Kiselev et al. | ............. | 376/195 |
| 7,235,216 B2 * | 6/2007 | Kiselev et al. | ............. | 422/159 |
| 2004/0028573 A1 * | 2/2004 | Schmitz et al. | ............ | 422/130 |
| 2005/0123475 A1 * | 6/2005 | Lim | .......................... | 424/1.11 |
| 2007/0217963 A1 * | 9/2007 | Elizarov et al. | ............ | 422/130 |
| 2008/0124274 A1 * | 5/2008 | Summerton | ................ | 424/1.69 |
| 2008/0193380 A1 * | 8/2008 | Dalton et al. | ............. | 424/1.89 |
| 2008/0294289 A1 * | 11/2008 | Lim | .......................... | 700/268 |

* cited by examiner

*Primary Examiner*—Jill Warden
*Assistant Examiner*—Dwayne K Handy
(74) *Attorney, Agent, or Firm*—Rosenberg, Klein & Lee

(57) ABSTRACT

A manufacturing method for $^{123}$I-ADAM and an automatic manufacturing device thereof are disclosed. The manufacturing process for $^{123}$I-ADAM consists of four steps-add [$^{123}$I] ammonium iodide solution, make oxidation reaction occur, terminate the reaction and neutralize the solution, filter and collect the filtrate. The automatic manufacturing device includes a plurality of units for taking each of the four steps that is disposed inside a chassis and is operated by automatic control. Users only need to put reactants into storage bottles respectively, turn on the power, and initiate the operation system, Then the preparation process of drugs for clinical diagnosis is finished within twenty minutes.

3 Claims, 2 Drawing Sheets

US 7,556,780 B1

DEVICE FOR $^{123}$I-ADAM AND AUTOMATIC MANUFACTURING DEVICE THEREOF

BACKGROUND OF THE INVENTION

The present invention relates to a manufacturing method and an automatic manufacturing device thereof, especially to a manufacturing method for $^{123}$I-ADAM and an automatic manufacturing device thereof applied to brain SPECT (single photon emission computed tomography) imaging in nuclear medicine.

Nuclear medicine is a branch of medicine pertaining to diagnostic, therapeutic and investigative use of radioactive chemical elements. Radiopharmaceuticals are made from radioactive nuclides (radioisotopes) that label various chemical elements. These chemicals enter specific organs in human bodies and involve in physiological mechanisms or biochemical reactions. By scintillation camera, distribution and metabolism of radioisotopes are learned so as to diagnose diseases. When diseases occur, changes happen firstly in Physiology and Biochemistry and anatomy the last. Thus, nuclear medical technology detects diseases in early stage, and about three to six months earlier than other tests. Earlier therapy leads to higher cure rates. Besides diagnostic use, radioisotopes are also applied to cancer therapy. A specific compound is labeled with therapeutic radioisotope and is sent to the position required for treatment. By high energy releasing from radioisotopes in short distance, the cancer cells are killed while normal cells are not affected. Thus side effects are reduced to minimum.

How are radiopharmaceuticals used? Nowadays radiopharmaceuticals are applied to various fields in medicine—ranging from Pediatrics, Psychiatry to Cardiology. The use of radiopharmaceuticals ranges broadly, covering almost all of important organs or systems. Besides specific, highly precise, highly accurate diagnostic radiopharmaceuticals, new therapeutic nuclear medicines have been developed rapidly. According to a report from US Biotech in 2003, the use of therapeutic nuclear medicines increases dramatically. Refer to a notice published by department of health, Executive Yuan, the top ten leading causes of death includes heart disease, Malignant neoplasms, liver diseases and Cerebrovascular disease. Thus the domestic research and development institutes are dedicated to early detection and intervention of various diseases. Preventive medicine is one of the most important fields to be developed in 21 century.

Nuclear medicine imaging visualizes a regional biochemical and physiological function in living humans by administration of radioactive agents. And a scintillation camera is used to detect distribution and metabolism of the radioactive agents inside human bodies for diagnosis of diseases. The radioactive agents in clinical use are divided into two categories—the first is single photon radionuclide that emits gamma ray with different energy levels while decaying and is imaging by Single Photon Emission Computed Tomography, (SPECT). The other is positron radionuclide that decays by emitting a positron. This positron quickly stops and annihilates with a nearby electron. In this annihilation interaction, two coincident 511 keV gamma rays are produced. Then Positron Emission Tomography (PET) is used to image.

Moreover, $^{123}$I-ADAM is disclosed by a professor of University of Pennsylvania, Hank F. Kung in 2000. The way he synthesizes the ADAM is used thiosalicylic acid and 2,5-dibromonitrobenzene as reactants and the final product is obtained after eight steps. The whole synthesis process takes quite a long time.

The present invention improves the manufacturing processes. There is no need to use High Performance Liquid Chromatographic Column for separating and purifying products. Thus preparation steps and time are saved. Moreover, not only the preparation time is reduced, the yield rate is also increased.

SUMMARY OF THE INVENTION

Therefore it is a primary object of the present invention to provide a manufacturing method for $^{123}$I-ADAM (Iodine-123 labeled 2-([2-([dimethylamino]methyl)phenyl]thio)-5-$^{123}$I-iodophenylamine) and an automatic manufacturing device thereof so that the radiochemical purity of products is over 90% and the average labeled yield rate achieves 60% (decay corrected).

It is another object of the present invention to provide a manufacturing method for $^{123}$I-ADAM and an automatic manufacturing device thereof that makes synthesis productivity of the products over 50%.

In order to achieve objects, the present invention uses a precursor -[2-((2-amino-4-tri-n-butyltinphenyl)thio)benzyl]dimethylamine (SnADAM) to synthesize $^{123}$I-ADAM. Firstly, $^{123}$I ammonium iodide solution is filled into a reaction bottle and is mixed with the precursor-SnADAM. Then oxidation agent is added into the mixture. Next the solution in the reaction bottle flows through a C-8 column for adsorption and the filtrate is discharged into a waste container. Elute the C-8 column with ethanol, the eluant is filled into an empty tube and then wash the column again in reverse direction. Then the eluant is filled into a receiving bottle, mixed with normal saline and vitamin C. At last, the solution is filtered by a filtration membrane to collect the final product.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
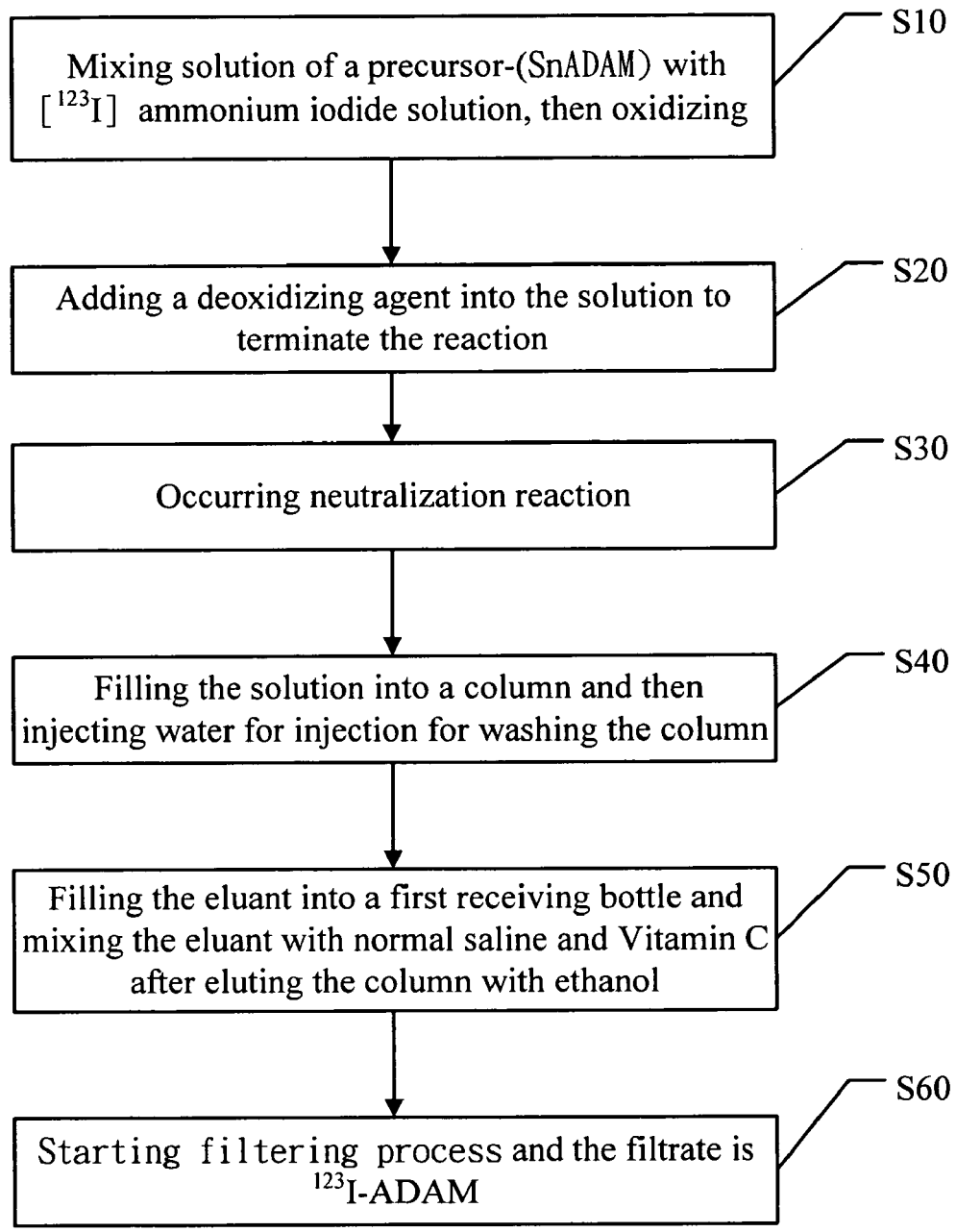
FIG. 1 is a flow chart of an embodiment of a manufacturing method according to the present invention.

Refer to the step S10 in FIG. 1, solution of a precursor -[2-((2-amino-4-tri-n-butyltinphenyl)thio)benzyl]dimethylamine (SnADAM) is mixed with ammonium iodide solution for being oxidized. Then take the step S20, add a deoxidizing agent into the solution to terminate the reaction. Next run the step S30, make the neutralization reaction occur. Refer to step S40, fill the solution into a column and then inject water for injection for washing the column. Then run the step S50, after eluting the column with ethanol, fill the eluant into a first receiving bottle and mix the eluant with normal saline and Vitamin C. At last, take the step S60, start the filtering process and the filtrate is $^{123}$I-ADAM.

Take an embodiment as an example. A precursor is mixed with a small amount of [$^{123}$I] ammonium iodide solution and hydrogen peroxide is added for initiating the oxidation reaction. After five minutes, sodium sulfite is added to terminate the reaction and then disodium hydrogen phosphate is added for neutralization. Next, the solution with pre-product is filled into a column for filtration. The filtrate is filled into a waste container and then wash the column with water for injection. Then elute the column with ethanol and the ethanol needs to be to-and-fro in the column for at least three times. Then the eluant is filled into a first receiving bottle, mixed with normal saline and vitamin C(j). Finally, the mixture is filtered by a sterile film with pore size such as 0.22 μm and then is filled into a second receiving bottle so as to obtain the final product required-$^{123}$I-ADAM.

Figure 2:
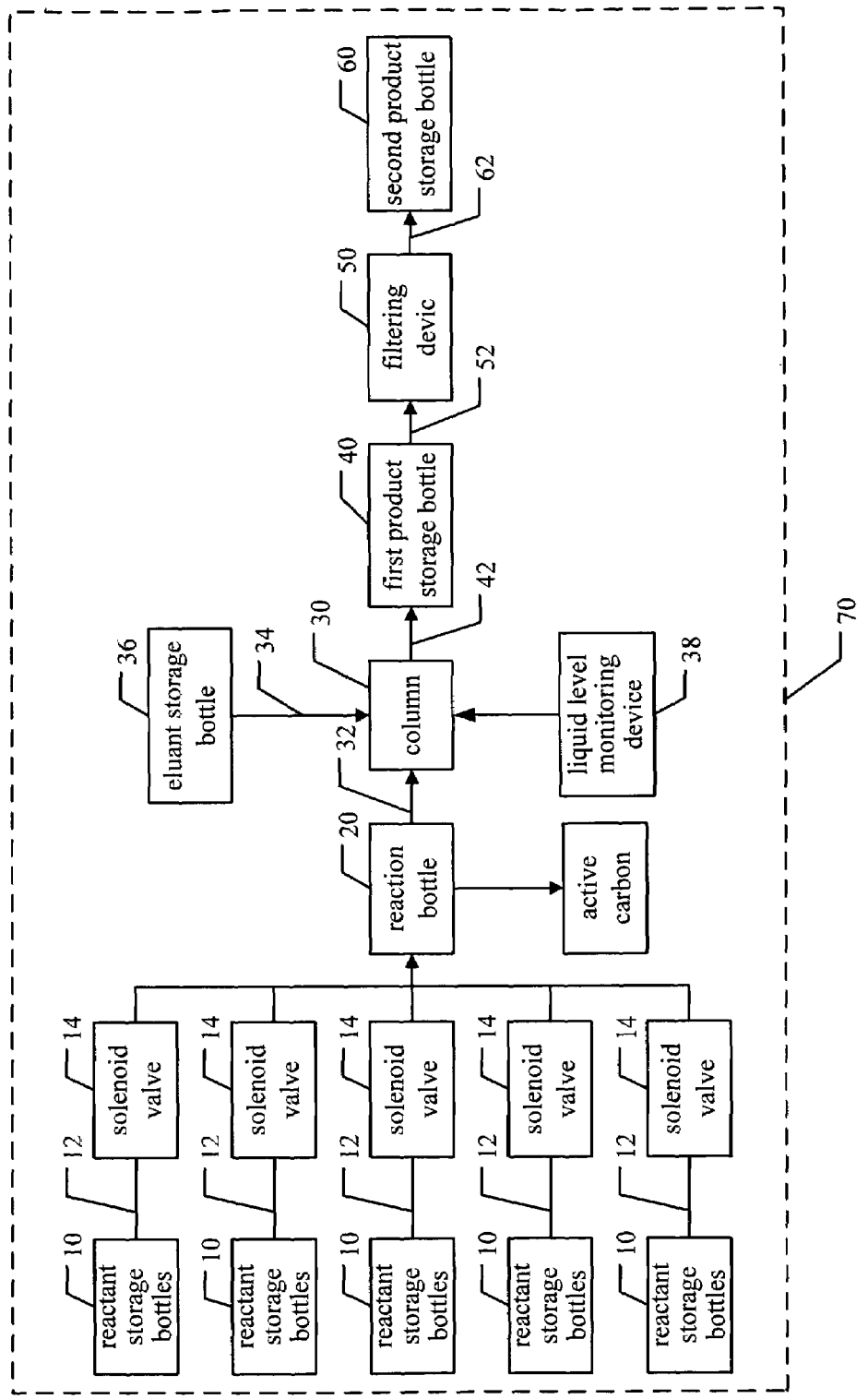
FIG. 2 is a block diagram of an embodiment of an automatic manufacturing device according to the present invention.

Refer to FIG. 2, an automatic manufacturing device includes a plurality of reactant storage bottles 10, a reaction bottle 20, a column 30, a first product storage bottle 40, a filtering device 50, a second product storage bottle 60.

The reaction bottle 20 connects with the reactant storage bottles 10 by a plurality of pipelines 12 and the pipelines 12 are disposed with a plurality of solenoid valves 14. Through a transport pipe 32, the column 30 connects with the reaction bottle 20 and it also joins with an eluant storage bottle 36 by an elution pipe 34. The first product storage bottle 40 is connected with the column 30 by a first collection pipe 42 while the filtering device 50 connects with the first product storage bottle 40 by a filtering pipe 52. The second product storage bottle 60 is connected with the filtering device 50 by a second collection pipe 62.

By a central processing unit 70 that controls the solenoid valves 14, the order and duration of reactants from the reactant storage bottles 10 to the reaction bottle 20 are controlled. Transportation of the pre-product from the reaction bottle 20 to the column 30 through the transport pipe 32 as well as the eluant from the eluant storage bottle 36 to the column 30 is controlled by the central processing unit 70. After elution, the eluant is sent to the first product storage bottle 40 through the first collection pipe 42 for storage. Then a first product in the first product storage bottle 40 is transported to the filtering device 50 by the filtering pipe 52 for being filtered. Then the solution is further transported into the second product storage bottle 60 through the second collection pipe 62 for storage of the second product inside the second product storage bottle 60. The way that the central processing unit 70 controls transportation of each pipe is a prior art. For example, through the design of valves in combination with a motor, transportation of liquid is controlled by a central processing unit or an electronic controller that controls each of the solenoid valves, receives measured pressure signal and connects with a personal computer so as to process the received signals and controls the whole manufacturing processes of the synthetic system according to the preset conditions. Thus an automatic or semi-automatic operation is achieved. The column 30 is further disposed with a liquid level monitoring device 38 for monitoring pre-product of the column 30 and learning liquid level of pipelines while eluting.

Take an embodiment as an example. The device according to the present invention should be arranged inside the lead room. The reactant storage bottles 10 respectively contain hydrogen peroxide, sodium sulfite, disodium hydrogen phosphate, pure water and [$^{123}$I] ammonium iodide solution. The reaction bottle is a bottom-pointed bottle with volume of 5 ml. The precursor weighted 100 μg needs to be set into the reaction bottle in advance and is dissolved in 50 μl ethanol. The [$^{123}$I] ammonium iodide solution is produced with nuclear reactions induced by high-energy proton beam generated by Cyclotron. In the beginning, carrier gas is filled into the reaction bottle and is mixed with the precursor. Then the hydrogen peroxide solution in the reactant storage bottle is conducted into the reaction bottle by the carrier gas and is aerated stirred for several seconds. In this embodiment, the carrier gas is nitrogen gas. Then leave the reaction bottle statically at the room temperature for five minutes. Next the sodium sulfite in the reactant storage bottle is filled into the reaction bottle by means of the carrier gas and is also aerated stirred for several seconds by to terminate the reaction. The disodium hydrogen phosphate in the reactant storage bottle is also transported into the reaction bottle by the carrier gas and is stirred for several seconds for neutralization. And the pre-product is generated. During the process, gas generated and exhausted from the reaction bottle is filtered by active charcoal so as to prevent gas with $^{123}$I from leaking into surroundings and causing pollution.

After that, the pre-product in the reaction bottle is conducted into the column for adsorption by the carrier gas. Depending on users needs, the carrier gas can be disposed with flow and pressure adjustment device. The filtrate is filled into the waste container. Subsequently, by carrier gas, part of the water for injection in the reactant storage bottle is drawn through the control valve, filled into the reaction bottle and stirred for seconds. Then the residual pre-product in the reaction bottle is conducted into the column and the filtrate is filled into the waste container. Next, by carrier gas, the rest water for injection in the reactant storage bottle passes through the control valve, filled into the column for washing out the un-reacted precursor or drugs. Only pre-product is adsorbed by the column.

In the next step, ethanol inside the reactant storage bottle passing through the control valve is filled into the column by means of the carrier gas for eluting the adsorbed pre-product. In order to enhance elution effects, ethanol inside the column is not flowing into the receiving bottle. Instead, the ethanol is filled into an empty tube by means of carrier gas in combination with the control valve. An infrared liquid level sensor between the column and the empty tube is used to monitor whether the ethanol runs out. Once the ethanol flows out of the column completely, the direction of the carrier gas is changed to the reverse direction so as to make the ethanol flows from the empty tube into the column. When the ethanol flows out of the empty tube completely, the direction of the carrier gas is changed once again so that the ethanol flows from the column into the empty tube. After repeating the above steps for about five times, the ethanol inside the column is filled into the receiving bottle by carrier gas. At last, the ore-product is transported from the first product storage bottle by the carrier gas, passing through the control valve, and filtered by a filtration membrane with pore size of 0.22 μm for purification. Thus the product of $^{123}$I-ADAM is obtained and received inside a sterile second product storage bottle.

It takes only twenty minutes from finishing preparation of reactants to obtaining the final product by an automatic manufacturing device according to the present invention. This matches requirements of the automatic synthesis system for manufacturing short half-life nuclear medicine. At room temperature, it takes five minutes for the precursor to react with hydrogen peroxide while filling the solution into the column for adsorption needs about 1 minute. Then it takes five minutes to wash the column. Another five minutes is to elute the column up and down with ethanol and the eluant is filled into the first product storage bottle. The filtering and collecting process needs about three minutes. After repeating tests for several times, it show that each step of the manufacturing process are carried out precisely according to commands from a control program. Variations in liquid level, pressure and radiation intensity inside pipelines are monitored during the whole manufacturing process. Moreover, the reaction finishes within twenty minutes.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An automatic manufacturing device of $^{123}$I-ADAM (Iodine-123 labeled 2-([2-dimethylamino]methyl)phenyl]thio)-5-$^{123}$I-iodophenylamine), comprising:
    a central processing unit controlling the operation of said automatic manufacturing device;
    a plurality of reactant storage bottles, each of said plurality of reactant storage bottles containing a reactant selected from a group consisting of [$^{123}$I] ammonium iodide solution, oxidizing agent, deoxidizing agent, neutralization agent, and water;
    a reaction bottle containing a SnADAM ([2-((2-amino-4-tri-n-butyltinphenyl)thio)benzyl]dimethylamine) precursor and connected with the reactant storage bottles by a plurality of pipelines, each of said plurality of pipelines being disposed with a respective solenoid valve, said central processing unit being coupled to each said respective solenoid valve to control an order and duration of supply of the reactants from said plurality of reactant storage bottles to said reaction bottle to produce a $^{123}$I-ADAM containing pre-product in said reaction bottle;
    a column connected to the output of said reaction bottle by a transport pipe to receive said $^{123}$I-ADAM containing pre-product from said reaction bottle under control of said control processing unit;
    an eluant storage bottle coupled to said column by an elution pipe, said eluant being added to said $^{123}$I-ADAM containing pre-product in said column in the controlled fashion to form a first product containing $^{123}$I-ADAM;
    a first product storage bottle connected with the column to store said first product transported from said column through a first collection pipe;
    a filtering device connected with the first product storage bottle by a filtering pipe to filter said first product and to generate a purified $^{123}$I-ADAM product; and
    a second product storage bottle connected with the filtering device by a second collection pipe to receive said purified $^{123}$I-ADAM product from said filtering device.

2. The device as claimed in claim 1, wherein the column further comprises a liquid level monitoring device coupled to the column for monitoring said pre-product in the column and liquid level of pipes while eluting.

3. The device as claimed in claim 1, wherein said oxidizing agent is hydrogen peroxide, said deoxidizing agent is sodium sulfite, and said neutralization agent is disodium hydrogen phosphate.

* * * * *